(12) United States Patent
Tissier et al.

(10) Patent No.: US 9,439,804 B2
(45) Date of Patent: Sep. 13, 2016

(54) METHOD AND SYSTEM FOR TREATMENT OF A BODY OF A MAMMAL IN CARDIAC ARREST

(76) Inventors: Renaud Tissier, Creteil (FR); Alain Berdeaux, Creteil (FR)

( * ) Notice: Subject to any disclaimer, the term of this patent is extended or adjusted under 35 U.S.C. 154(b) by 663 days.

(21) Appl. No.: 13/039,415

(22) Filed: Mar. 3, 2011

(65) Prior Publication Data
US 2012/0226337 A1 Sep. 6, 2012

(51) Int. Cl.
*A61F 7/12* (2006.01)
*A61F 7/00* (2006.01)

(52) U.S. Cl.
CPC .......... *A61F 7/12* (2013.01); *A61F 2007/0063* (2013.01); *A61F 2007/0069* (2013.01)

(58) Field of Classification Search
CPC . A61F 7/0085; A61F 7/12; A61F 2017/0063
USPC .................. 607/105; 128/200.24, 204.15
See application file for complete search history.

(56) References Cited

U.S. PATENT DOCUMENTS

| | | | | |
|---|---|---|---|---|
| 5,308,320 A | * | 5/1994 | Safar et al. ................. | 604/6.14 |
| 5,335,650 A | * | 8/1994 | Shaffer et al. ........... | 128/200.24 |
| 5,490,498 A | * | 2/1996 | Faithfull et al. ......... | 128/203.12 |
| 5,492,109 A | * | 2/1996 | Hirschl et al. ............ | 128/201.21 |
| 5,540,225 A | * | 7/1996 | Schutt ...................... | 128/207.15 |
| 5,655,521 A | * | 8/1997 | Faithfull et al. ......... | 128/203.12 |
| 5,706,830 A | * | 1/1998 | Parker ...................... | 128/203.12 |
| 5,853,003 A | * | 12/1998 | Faithfull et al. ......... | 128/203.12 |
| 5,927,273 A | * | 7/1999 | Federowicz et al. .... | 128/200.24 |
| 6,041,777 A | * | 3/2000 | Faithfull et al. ......... | 128/200.24 |
| 6,346,552 B1 | * | 2/2002 | Albrecht .................. | 514/771 |
| 6,694,977 B1 | * | 2/2004 | Federowicz et al. .... | 128/204.18 |
| 6,983,749 B2 | * | 1/2006 | Kumar et al. ............ | 128/204.15 |
| 7,201,163 B2 | * | 4/2007 | Jiang et al. ............... | 128/200.21 |
| 7,726,311 B2 | * | 6/2010 | Robert et al. ............. | 128/205.19 |
| 2004/0134486 A1 | * | 7/2004 | Robert et al. ............. | 128/200.13 |
| 2007/0021808 A1 | * | 1/2007 | Rojas ........................ | 607/105 |
| 2009/0076573 A1 | * | 3/2009 | Burnett et al. ............ | 607/105 |
| 2012/0095537 A1 | * | 4/2012 | Hall et al. ................. | 607/105 |
| 2013/0296983 A1 | * | 11/2013 | Keller et al. .............. | 607/105 |

FOREIGN PATENT DOCUMENTS

EP 1424090 11/2003

OTHER PUBLICATIONS

Kaisers et al., "Liquid ventilation", 2003, British Journal of Anaesthesia, 91(1), 143-151.*
Sehgal et al., "Liquid Ventilation", 2005, The Indian Journal of Chest Disease & Allied Sciences, 47, 187-192.*

* cited by examiner

*Primary Examiner* — Ronald Hupczey, Jr.
(74) *Attorney, Agent, or Firm* — McAndrews Held and Malloy

(57) ABSTRACT

Method for treatment of a body of a mammal in cardiac arrest, comprising the step of performing a therapeutic hypothermia of the body after the cardiac arrest has occurred, said therapeutic hypothermia comprising:
  cooling the body to a target temperature during a cooling time period, said cooling being performed by total liquid ventilation which comprises alternately filling lungs of the body with a cooling liquid and removing from the lungs said cooling liquid,
  maintaining the body at the target temperature for a hypothermia duration.

5 Claims, 8 Drawing Sheets

METHOD AND SYSTEM FOR TREATMENT OF A BODY OF A MAMMAL IN CARDIAC ARREST

FIELD OF THE INVENTION

The invention relates to a method and a system for treatment of a body of a mammal in cardiac arrest.

BACKGROUND OF THE INVENTION

Although not limited thereto, the invention applies to the treatment of "Sudden death" or out-of-hospital cardiac arrest which still represents a major public health issue. Its annual incidence reaches approximately 50,000 to 60,000 cases in France. A minor part of those patients can be resuscitated and further survive. They often exhibit severe neurological sequels and other dysfunctions resulting from the cardiac arrest. In addition to the dramatic consequences for these patients, this applies a high socioeconomic cost when the patients should be maintained in critical care unit for a long term.

Institution of mild "therapeutic" hypothermia (32-34° C.) during 24 to 36 hours after resuscitation is known to improve survival and neurological recovery in comatose survivors of cardiac arrest ("Treatment of comatose survivors of out-of-hospital cardiac arrest with induced hypothermia", Bernard•S A, Gray T W, Buist M D, Jones B M, Silvester W, Gutteridge G, Smith K, N Engl J Med, 2002; 346:557-563; "Mild therapeutic hypothermia to improve the neurologic outcome after cardiac arrest", The Hypothermia After Cardiac Arrest Study Group, N Engl J Med. 2002; 346:549-556).

However, experimental studies in dogs ("Mild hypothermia during prolonged cardiopulmonary cerebral resuscitation increases conscious survival in dogs", Nozari A, Safar P, Stezoski S W, Wu X, Henchir J, Radovsky A, Hanson K, Klein E, Kochanek P M, Tisherman S A, Crit Care Med, 2004; 32:2110-2116; "Critical time window for intra-arrest cooling with cold saline flush in a dog model of cardiopulmonary resuscitation", Nozari A, Safar P, Stezoski S W, Wu X, Kostelnik S, Radovsky A, Tisherman S, Kochanek P M, Circulation 2006; 113:2690-2696), pigs ("A comparison between head cooling begun during cardiopulmonary resuscitation and surface cooling after resuscitation in a pig model of cardiac arrest", Guan J, Barbut D, Wang H, Li Y, Tsai M S, Sun S, Inderbitzen B, Weil M H, Tang W, Crit Care Med, 2008; 36:S428-433; "Rapid head cooling initiated coincident with cardiopulmonary resuscitation improves success of defibrillation and post-resuscitation myocardial function in a porcine model of prolonged cardiac arrest", Tsai M S, Barbut D, Tang W, Wang H, Guan J, Wang T, Sun S, Inderbitzen B, Weil M H, J Am Coll Cardiol, 2008; 51:1988-1990) and rodents ("Intra-arrest cooling with delayed reperfusion yields higher survival than earlier normothermic resuscitation in a mouse model of cardiac arrest", Zhao D, Abella B S, Beiser D G, Alvarado J P, Wang H, Hamann K J, Hoek T L, Becker L B, Resuscitation, 2008; 77:242-249; "Intra-arrest cooling improves outcomes in a murine cardiac arrest model", Abella B S, Zhao D, Alvarado J, Hamann K, Vanden Hoek T L, Becker L B, Circulation, 2004; 109:2786-2791) demonstrated that the neuroprotection afforded by hypothermia was related to the rapidity in body temperature decrease after resuscitation. When achieved rapidly, hypothermia could also be beneficial for other organs since it can be, for example, also potently cardioprotective during myocardial ischemia ("Hypothermia during reperfusion limits no-reflow injury in a rabbit model of acute myocardial infarction", Hale S L, Dae M W, Kloner R A, Cardiovasc Res, 2003; 59:715-722; "Second window of protection against infarction in conscious rabbits: real or artifactual", Miki T, Swafford A N, Cohen M V, Downey J M, J Mol Cell Cardiol, 1999; 31:809-816; "Rapid cooling preserves the ischaemic myocardium against mitochondrial damage and left ventricular dysfunction", Tissier R, Couvreur N, Ghaleh B, Bruneval P, Lidouren F, Morin D, Zini R, Bize A, Chenoune M, Belair M F, Mandet C, Douheret M, Dubois-Rande J L, Parker J C, Cohen M V, Downey J M, bordeaux, A Cardiovasc Res, 2009; 83:345-353; "The small chill: mild hypothermia for cardioprotection?", Tissier R, Chenoune M, Ghaleh B, Cohen M V, Downey J M, Berdeaux A, Cardiovasc Res, 2010; 88:406-414).

Accordingly, many strategies were proposed to afford such a rapid hypothermia, including intravenous infusion of cold fluid ("Cold saline infusion and ice packs alone are effective in inducing and maintaining therapeutic hypothermia after cardiac arrest", Larsson I M, Wallin E, Rubertsson S, Resuscitatio, 2010; 81:15-19), endovascular or intranasal cooling ("Induction of mild systemic hypothermia with endovascular cooling during primary percutaneous coronary intervention for acute myocardial infarction", Dixon S R, Whitbourn R J, Dae M W, Grube E, Sherman W, Schaer G L, Jenkins J S, Bairn D S, Gibbons R J, Kuntz R E, Popma J J, Nguyen T T, O'Neill W W, J Am Coll Cardiol, 2002; 40:1928-1934; "Survival and neurological outcomes after nasopharyngeal cooling or peripheral vein cold saline infusion initiated during cardiopulmonary resuscitation in a porcine model of prolonged cardiac arrest", Yu T, Barbut D, Ristagno G, Cho J H, Sun S, Li Y, Weil M H, Tang W, Crit Care Med, 2010; 38:916-921; "Feasibility of intra-arrest hypothermia induction: A novel nasopharyngeal approach achieves preferential brain cooling", Boller M, Lampe J W, Katz J M, Barbut D, Becker L B, Resuscitation, 2010; 81:1025-1030).

Besides, total liquid ventilation that alternatively instillates and removes a tidal volume of perfluorocarbon from the lungs has already been used to decrease rapidly the left atrial temperature in rabbits. This was associated with a very potent protection against myocardial infarction and subsequent contractile dysfunction in animal models of coronary artery occlusion ("Rapid cooling of the heart with total liquid ventilation prevents transmural myocardial infarction following prolonged ischemia in rabbits", Chenoune M, Lidouren F, Ghaleh B, Couvreur N, Dubois-Rande J-L, Berdeaux A, Tissier R, Resuscitation, 2010; 81:359-362; "Total liquid ventilation provides ultra-fast cardioprotective cooling", Tissier R, Hamanaka K, Kuno A, Parker J C, Cohen M V, Downey J M, J Am Coll Cardiol, 2007; 49:601-605). In a swine model of ventricular fibrillation, liquid ventilation also induced a rapid convective cooling that further improves the chances for subsequent resumption of spontaneous circulation ("Intra-arrest hypothermia: both cold liquid ventilation with perfluorocarbons and cold intravenous saline rapidly achieve hypothermia, but only cold liquid ventilation improves resumption of spontaneous circulation", Riter H G, Brooks L A, Pretorius A M, Ackermann L W, Kerber R E, Resuscitation, 2009; 80:561-566; "Liquid ventilation with perfluorocarbons facilitates resumption of spontaneous circulation in a swine cardiac arrest model", Staffey K S, Dendi R, Brooks L A, Pretorius A M, Ackermann L W, Zamba K D, Dickson E, Kerber R E, Resuscitation, 2008; 78:77-84).

However, the effect of hypothermic total liquid ventilation (TLV) instituted after cardiac arrest has never been investigated for post-cardiac arrest dysfunctions.

The invention aims to improve the protection against the post-cardiac arrest dysfunctions.

SUMMARY OF THE INVENTION

To this end, the invention provides a method for treatment of a body of a mammal in cardiac arrest, comprising the step of performing a therapeutic hypothermia of the body after the cardiac arrest has occurred, said therapeutic hypothermia comprising:

cooling the body to a target temperature during a cooling time period, said cooling being performed by total liquid ventilation which comprises alternately filling lungs of the body with a cooling liquid and removing from the lungs said cooling liquid, maintaining the body at the target temperature for a hypothermia duration.

The therapeutic hypothermia by total liquid ventilation uses the lungs as heat exchangers to afford a very rapid, controlled and generalized cooling of the body of the mammal. In particular, the cooling time period may be less than 10 minutes, especially of about 5 minutes. The total liquid ventilation further maintains normal gas exchanges during cooling thereby providing a protection of the lung integrity and of other main organs of the body such as the heart, the brain, the liver and the kidneys.

The method for treatment may further comprise the step of attempting resuscitation of the mammal after the cardiac arrest has occurred. The therapeutic hypothermia may then be begun after, during or before the step of attempting resuscitation.

On one hand, the step of attempting resuscitation may comprise resumption of spontaneous circulation. The invention makes it possible to improve survival of the mammal and to limit the risks of neurological sequels and dysfunctions of the other main organs, such as the aforementioned heart, lungs, liver and kidneys.

On the other hand, when unfortunately no resumption of spontaneous circulation occurs, the invention makes it possible to preserve the main organs in view of a possible transplantation.

The therapeutic hypothermia may further comprise removing the cooling liquid after the cooling time period has elapsed, the maintenance of the body at the target temperature being performed by conventional gas ventilation.

The method for treatment may further comprise the step of rewarming the body after the hypothermia duration has elapsed.

In a particular embodiment, the mammal is an adult human.

The invention also provides a system for treatment of a body of a mammal in cardiac arrest, comprising:

a cooling device adapted to cool the body to a target temperature during a cooling time period, said cooling device being adapted to perform total liquid ventilation and comprising:
  a reservoir filled with a cooling liquid,
  a pumping arrangement adapted to alternately fill lungs of the body with the cooling liquid and remove from the lungs said cooling liquid,
a temperature maintaining device adapted to maintain the body at the target temperature for a hypothermia duration.

In particular, the cooling liquid may be chosen in the group consisting of perfluorocarbons.

The system for treatment may further comprise at least one resuscitation apparatus adapted to attempt resuscitation of the mammal.

BRIEF DESCRIPTION OF THE DRAWINGS

Other objects and advantages of the invention will emerge from the following disclosure of a particular embodiment of the invention given as non limitative example, the disclosure being made in reference to the enclosed drawings in which.

DETAILED DESCRIPTION

The invention provides a system for treatment of a body of a mammal in cardiac arrest. The system aims to reduce dysfunctions resulting from cardiac arrest in animals, of small size (especially less than 40 kg) and large size (especially over 40 kg), and in humans, child or adult. To that end, the system is adapted to perform a therapeutic hypothermia comprising a cooling of the body to a target temperature during a cooling time period and a maintaining of the body at the target temperature for a hypothermia duration.

Figure 1A:
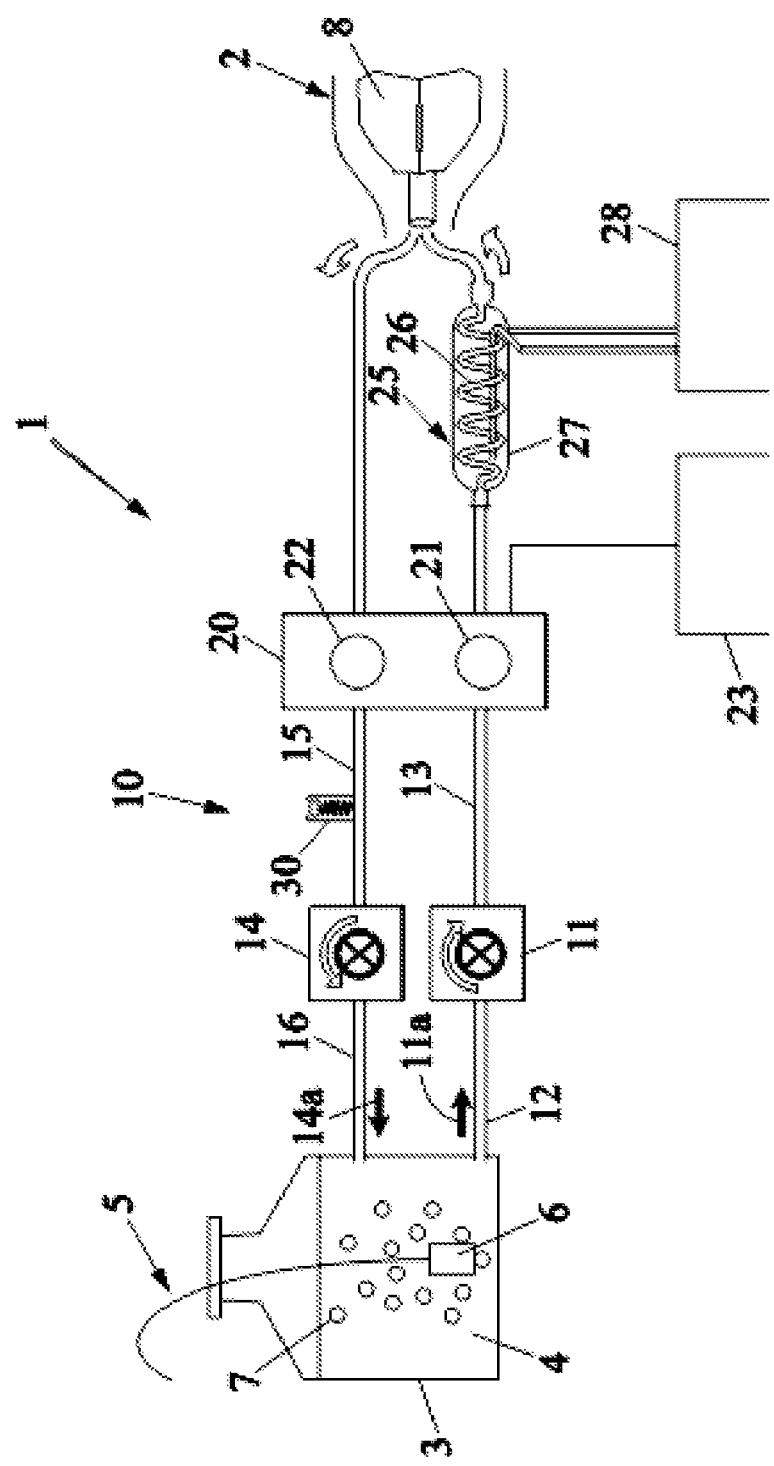
FIG. 1A is a schematic representation of a cooling device of a system for treatment of a body of a mammal in cardiac arrest according to an embodiment of the invention.

FIG. 1A schematically illustrates a liquid ventilator 1 of the system according to an embodiment of the invention.

In particular, the liquid ventilator forms a cooling device adapted to perform total liquid ventilation, sometimes hereafter referred to as TLV, to cool the body, and in particular the heart-lungs block 2, to the target temperature, especially comprised between about 32° C. and about 34° C., and especially equal to about 32° C., in a very short cooling time period, especially less than 10 minutes, in particular within about 5 minutes.

To this end, the liquid ventilator 1 comprises a reservoir 3 filled with a cooling liquid 4. Advantageously, the cooling liquid is chosen in the group consisting of perfluorocarbons which are biocompatible and well tolerated by the body and have suitable viscosity, high thermal conductivity and excellent gas-carrier capacity for oxygenation and carbon dioxide removal. In this respect, for oxygenation during cooling, an oxygen supplier 5 is provided to add oxygen 7 to the cooling liquid 4 through a pipe 6 placed within the reservoir 3 immersed in the cooling liquid 4.

The liquid ventilator 1 also comprises a pumping arrangement 10 comprising:
- an inflow pump 11 adapted to draw the cooling liquid 4 from an upstream pipe 12 connected to the reservoir 3, as shown by arrow 11a on FIG. 1A, and to push the cooling liquid 4 in a downstream pipe 13,
- an outflow pump 14 adapted to draw the cooling liquid 4 from an upstream pipe 15 and to push the cooling liquid 4 in a downstream pipe 16, for example connected to the reservoir 3, as shown by arrow 14a on FIG. 1A.

The downstream pipe 13 of the inflow pump 11 and the upstream pipe 15 of the outflow pump 14 are connected to a selector 20 so as to selectively push and draw the cooling liquid 4 downstream of the selector 20. For example, the selector 20 comprises an inflow valve 21 and an outflow valve 22, in particular of solenoid type, mounted respectively on the downstream pipe 13 of the inflow pump 11 and the upstream pipe 15 of the outflow pump 14. The openings and closings of the inflow valve 21 and outflow valve 22 are electronically controlled by a central unit 23.

The upstream pipe 15 of the outflow pump 14 may be provided with a vacuum control 30.

To control the temperature of the cooling liquid 4 in the downstream pipe 13 of the inflow pump 11, a heat exchanger 25 is provided. In particular, the heat exchanger 25 comprises a serpentine 26 formed on a part of the downstream pipe 13 of the inflow pump 11 downstream of the selector 20. An outer casing 27 connected to a supply 28 of water at a controlled temperature surrounds the serpentine 26 so as to exchange heat, and especially to absorb heat, with the cooling liquid 4 circulating in the serpentine 26. The controlled temperature is chosen to set the cooling liquid 4 at the target temperature.

An outlet of the downstream pipe 13 of the inflow pump 11, downstream of the serpentine 26, and an inlet of the upstream pipe 15 of the outflow pump 14 are connected to the respiratory system of the mammal, for example through an endotracheal tube.

In doing so, the pumping system can alternately:
- instill the cooling liquid 4, at the target temperature, in the lungs 8 so as to fill the lungs 8 with the cooling liquid 4, the inflow pump 11 being turned on, the inflow valve 21 being opened and the outflow valve 22 being closed, and
- remove the cooling liquid 4 from the lungs 8, the outflow pump 14 being turned on, the outflow valve 22 being opened and the inflow valve 21 being closed.

In particular, the inflow 11 and outflow 14 pumps are adapted to instill and remove a tidal volume of cooling liquid 4 corresponding to the weight of the mammal on which the treatment is performed. Besides, the instillation and the removal of the cooling liquid 4 are performed during a cooling time period at a suitable respiratory rate.

The invention is not limited to the above disclosed pumping arrangement comprising two separate pumps connected to corresponding valves. As an alternative, a single pump suitably controlled could also be provided.

Figures 1B, 1C:
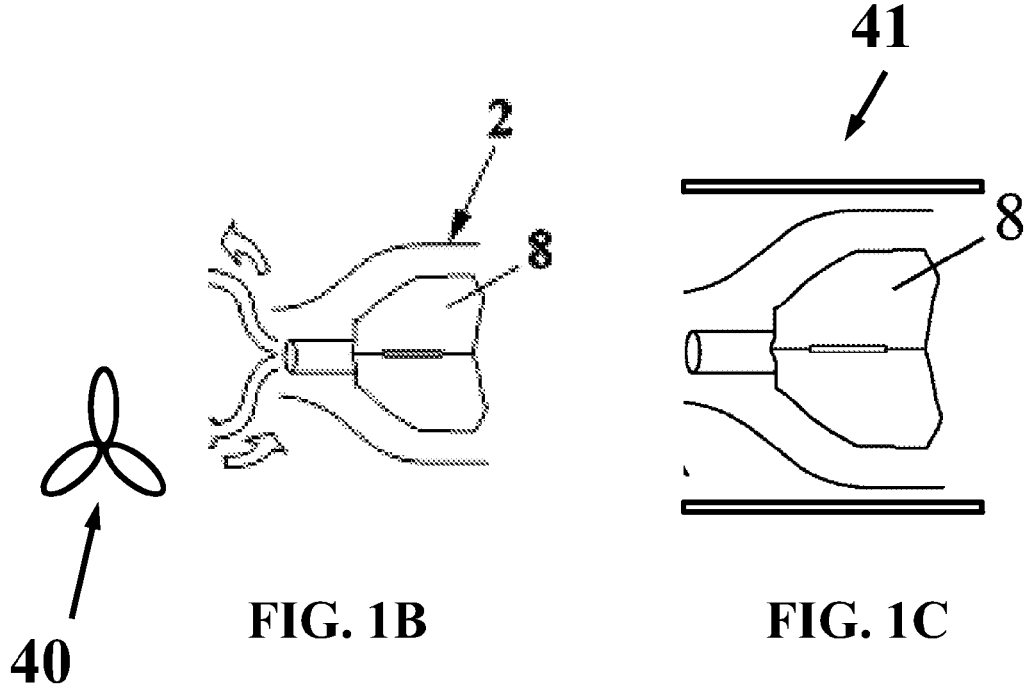
FIG. 1B is a schematic representation of a temperature maintaining device of the system for treatment of a body of a mammal in cardiac arrest according to an embodiment of the invention.
FIG. 1C is a schematic representation of a temperature maintaining device of the system for treatment of a body of a mammal in cardiac arrest according to another embodiment of the invention.

The system according to the invention also comprises a temperature maintaining device adapted to maintain the body at the target temperature for the hypothermia duration. For example, as shown in FIG. 1B, the temperature maintaining device may comprise a mechanical ventilator 40 connected to the tube to perform conventional gas ventilation, especially though instillation of oxygen at a desired temperature. Where needed, the temperature maintaining device may comprise any other suitable means, such as cold blankets 41 shown in FIG. 10, to have the body maintained at the target temperature.

Figure 1D:
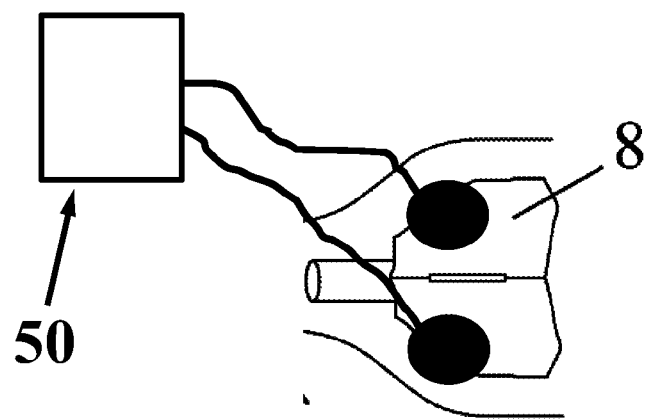
FIG. 1D is a schematic representation of a resuscitation apparatus of the system for treatment of a body of a mammal in cardiac arrest according to an embodiment of the invention, FIG. 2 provides a diagram illustrating the experimental protocol of a study implementing a method for treatment of a body of a mammal in cardiac arrest according to an embodiment of the invention, the study being performed on different experimental groups of rabbits, namely groups $Control_5$, and $TLV_5$, composed of rabbits submitted to 5 minutes of cardiac arrest under control conditions or with hypothermic total liquid ventilation after resumption of spontaneous circulation, groups $Control_{10}$, and $TLV_{10}$, composed of rabbits submitted to 10 minutes of cardiac arrest under control conditions or with hypothermic total liquid ventilation after resumption of spontaneous circulation, FIG. 3 provides graphs illustrating the evolution of oesophageal, tympanic and rectal temperatures as a function of time in the different experimental groups of the study, FIG. 4 provides graphs illustrating Blood pH, partial pressure of carbon dioxide $pCO_2$ and partial pressure of oxygen $pO_2$ before cardiac arrest and 15 minutes and 180 minutes after cardiac arrest in the different experimental groups of the study (*$p<0.05$ Vs corresponding Control; n=10 in each experimental group), FIG. 5 in which panels A and B provide neurological dysfunction scores at days 1, 2 and 7 following resuscitation in the different experimental groups of the study, open circles representing individual scores and thick lines representing the median value of the corresponding groups, and panels C and D provide Kaplan-Meyer survival curves in the different experimental groups of the study (*$p<0.05$ Vs corresponding Control), FIG. 6 in which panel A provides examples of normal or pathological histological appearances of kidney, liver and lungs of rabbits in the different experimental groups of the study, arrows representing disorders, and panel B provides histological scores of alteration in kidney, liver and lungs of rabbits in the different experimental groups of the study, wherein for lungs, two separate scores for cardiogenic lesions and infection complications are assessed, open circles representing individual scores and thick lines representing the median value of corresponding groups (*$p<0.05$ Vs corresponding Control), FIG. 7 in which panel A provides examples of normal or pathological histological appearances of the brain and the heart of rabbits in the different experimental groups of the study, arrows representing disorders, and panel B provides histological scores of alteration in the brain and heart of rabbits in the different experimental groups of the study, open circles representing individual scores and thick lines representing the median value of the corresponding groups ($*p<0.05$ Vs corresponding Control), FIG. 8 provides graphs illustrating Troponin I blood levels (left panel) and myocardial caspase 3 activity (right panel) in two different groups of the study, namely $Control_{10'}$ and $TLV_{10'}$, Caspase 3 activity assays being performed in myocardial samples withdrawn 60 minutes after the cardiac arrest episode ($*p<0.05$ Vs corresponding Control; n=8 in each experimental group).

Besides, as shown in FIG. 1D, the system according to the invention may further comprise at least one resuscitation apparatus 50 adapted to attempt resuscitation of the mammal. The attempts for resuscitation of the mammal may comprise cardiac massage, electrics attempt of defibrillation and intravenous administration of epinephrine, the resuscitation apparatus comprising the elements adapted to perform these attempts.

The system according to the invention may further be completed by a rewarming device, comprising for example infra-red lights and thermal pads, to rewarm the body after hypothermia has been performed.

The whole system may be controlled by a monitoring unit adapted to measure, and possibly to process, different data related to the treatment, such as temperatures of different parts of the body, electrocardiogram, arterial pressure in the body and others.

The invention also provides a method for treatment of a body of a mammal in cardiac arrest. As for the system, the method aims to reduce dysfunctions resulting from cardiac arrest both in animals and in humans by cooling the body, and in particular the heart-lungs block, to the target temperature in the very short cooling time period, and by maintaining the body at the target temperature for the hypothermia duration.

The mammal has undergone the cardiac arrest for a cardiac arrest time period, especially of less than 15 minutes, for example 5 to 10 minutes.

In a particular embodiment, after the cardiac arrest has occurred, i.e. after the cardiac arrest time period has elapsed, a step of attempting resuscitation of the mammal is performed by any suitable manner comprising cardiac massage, electric attempt of defibrillation and intravenous administration of epinephrine.

In cases where the attempt for resuscitation of the mammal is successful and is accompanied by resumption of spontaneous circulation, after the step of attempting resuscitation and after spontaneous circulation has been restored, a therapeutic hypothermia implementing total liquid ventilation is begun to cool the body to the target temperature.

The total liquid ventilation is implemented for example through a liquid ventilator 1 of the type disclosed above in relation to FIG. 1A.

As indicated above, the total liquid ventilation is performed by alternately filling the lungs 8 with the cooling liquid 4 and removing from the lungs 8 the cooling liquid 4. The total liquid ventilation uses the lungs 8, through which the whole blood flows in a short time period, as a heat exchanger to cool the body rapidly.

After the cooling time period has elapsed, the cooling liquid 4 is removed from the lungs 8 and the total liquid ventilation is followed by maintenance of the body at the target temperature, for example by conventional gas ventilation, for the hypothermia duration.

After the hypothermia duration has elapsed, the body is then rewarmed in any suitable manner implementing for example the above disclosed infra-red lights and thermal pads.

In other embodiments, the therapeutic hypothermia may be begun during or before the step of attempting resuscitation.

Besides, in cases where no resumption of spontaneous circulation or even where no attempt for resuscitation is performed, the therapeutic hypothermia may be performed to protect the body and the main organs against post cardiac arrest dysfunctions in view of a possible transplantation.

A study implementing the above disclosed method is now disclosed in relation to FIGS. 2 to 8.

The main purpose of the hereafter disclosed study is to investigate the long term effect of ultrafast cooling induced by total liquid ventilation (TLV) in a rabbit model of post-cardiac arrest dysfunction following ventricular fibrillation and resuscitation. Neurological, cardiac, pulmonary, liver and kidney potential dysfunctions were especially focused on. The study also aimed to investigate whether ultra-fast cooling can protect the heart through an early inhibition of cardiac cell death. The latter point was also critical to further support the relevance of very fast cooling to limit the subsequent dysfunction following cardiac arrest.

Methods

The animal instrumentation and ensuing experiments were conducted in accordance with French official regulations (agreement A94-046-13) after approval by the local ethical committee. The investigation conformed to the *Guide for the Care and Use of Laboratory Animals* published by the US National Institutes of Health.

Animal Preparation

New Zealand rabbits (3.0-3.5 kg) were anesthetized using zolazepam, tiletamine and pentobarbital (all 20-30 mg/kg i.v.). They were intubated and mechanically ventilated. After administration of pancuronium bromide (200 μg/kg i.v.), two electrodes were implanted upon the chest and inserted into the esophagus for subsequent induction of ventricular fibrillation. Rectal, esophageal and tympanic temperatures were continuously monitored using thermal probes (Harvard Apparatus, Paris, France). Throughout the protocol, external electrocardiogram was recorded, as well as arterial blood pressure from a catheter implanted into the ear artery. Data were digitalized and analyzed using the data acquisition software HEM v3.5 (Notocord, Croissy-sur-Seine, France).

Cardiac Arrest and Cardiopulmonary Resuscitation

After animal preparation and subsequent stabilisation, ventricular fibrillation was induced by passing an alternative current (10 V, 4 mA) between the implanted electrodes. Mechanical ventilation was stopped at the onset of fibrillation and throughout the subsequent period of cardiac arrest. After either 5 or 10 min of untreated fibrillation, cardiopulmonary resuscitation was started using cardiac massage (about 200 beats/min), electric attempt of defibrillation (5-10 J/kg) and intravenous administration of epinephrine (15 μg/kg i.v.). Resumption of spontaneous circulation (ROSC) was considered as an organized cardiac rhythm associated with a mean arterial pressure above 40 mmHg during at least 1 minute. After ROSC, administration of epinephrine was further permitted during a maximum of 7 hours at a dosage appropriately adjusted to maintain mean arterial pressure at about 80 mmHg. Mechanical ventilation was continued until weaning and awakening of the animals. Rabbits subsequently returned to their cage for a survival follow-up. They received antibiotics (enrofloxacine, 5 mg/kg i.m.) during 7 days and analgesics (buprenorphine, 30 μg/kg s.c.) during 3 days.

Experimental Protocol

Figure 2:
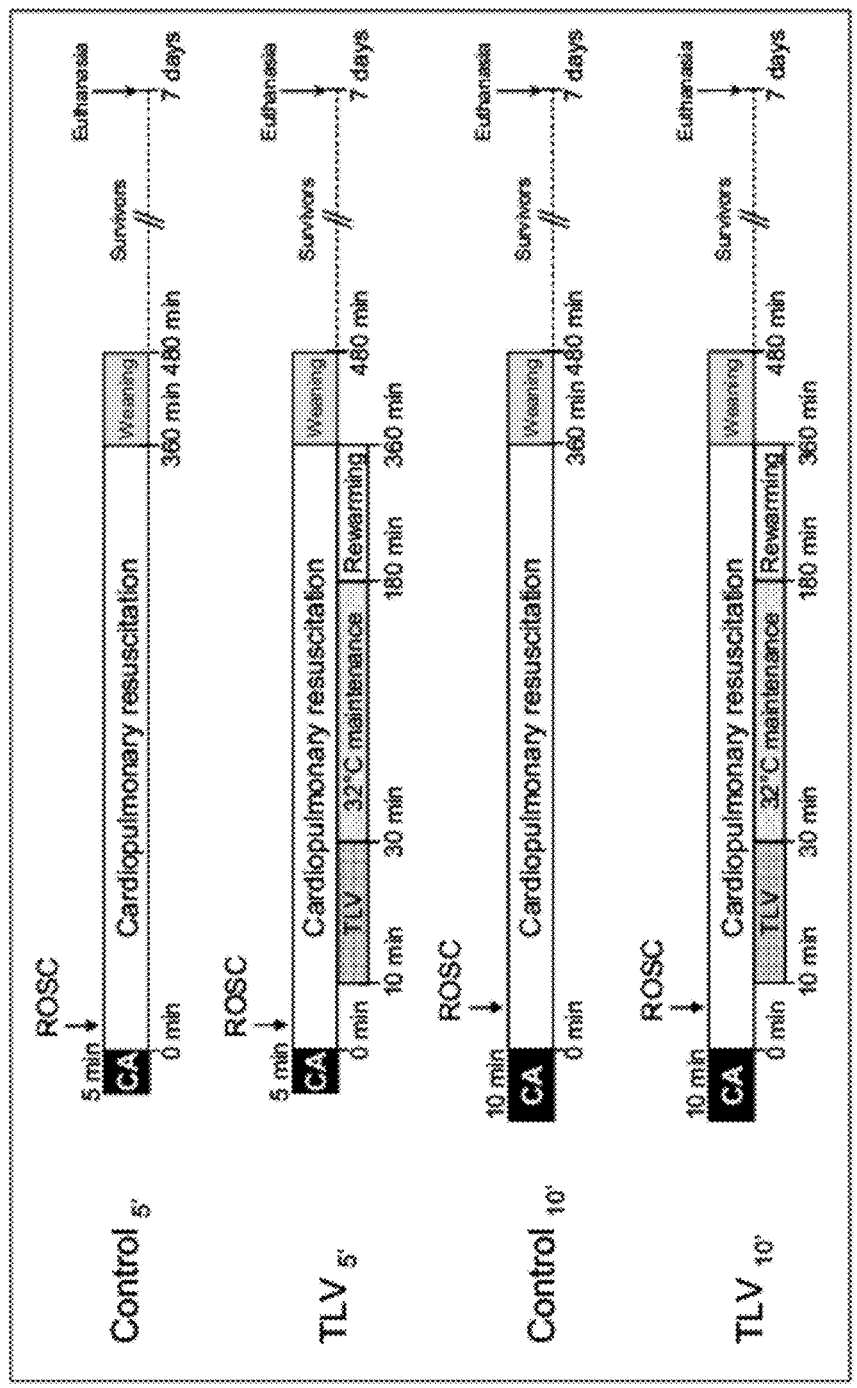

The experimental protocol of the study is illustrated on FIG. 2, in which CA means cardiac arrest, TLV means total liquid ventilation and ROSC means resumption of spontaneous circulation.

As shown in FIG. 2, rabbits randomly underwent either 5 or 10 minutes of cardiac arrest with subsequent cardiopulmonary resuscitation under normothermic conditions (Control$_5$, and Control$_{10}$, groups, respectively) or with hypothermia induced by TLV (TLV$_5$, and TLV$_{10}$, groups, respectively). In these last two groups, TLV was started at the $10^{th}$ minute following cardiopulmonary resuscitation (i.e., after ROSC) by filling the lung with 10 ml/kg of perfluorocarbon (Fluorinert, 3M, Cergy, France) and then connecting the endotracheal tube to the above disclosed liquid ventilator. The ventilator was set to a tidal volume of about 7 to 10 ml/kg of body weight with a respiratory rate of 6 breaths/minute. The temperature of the heat exchanger was adjusted to maintain esophageal and tympanic temperatures at a target temperature of about 32° C. After 20 minutes of TLV and achievement of the hypothermic target temperature, the perfluorocarbon was evacuated from the lungs by gravity and the endotracheal tube was again connected to a conventional mechanical ventilator. Hypothermia was further maintained at 32° C. during 3 hours, if necessary using cold blankets. Animals were subsequently rewarmed using infra-red lights and thermal pads until weaning from conventional ventilation and awakening. Animals were housed in a closed cage enriched in $O_2$ during 2-3 days to avoid hypoxic episodes.

In order to further investigate the effects of hypothermic TLV, additional rabbits were included in the $Control_{10'}$ and $TLV_{10'}$ groups, respectively. These animals were euthanized one hour after the cardiac arrest episode for collection of myocardial and blood samples for caspase activity assays and measurement of circulating troponin I, respectively.

Neurological and Cardiac Dysfunction Assessment

Neurological dysfunction was evaluated daily in surviving animals using a clinical score previously validated in rabbits ("Hypothermia prevents ischemia-induced increases in hippocampal glycine concentrations in rabbits", Baker A J, Zornow M H, Grafe M R, Scheller M S, Skilling S R, Smullin D H, Larson A A, Stroke, 1991; 22:666-673), as shown in Supplemental Table 1 providing a rabbit neurological deficit grading scale (0-10%=normal; 100%=brain death).

SUPPLEMENTAL TABLE 1

| | | Maximum score |
|---|---|---|
| Level of conciousness | | |
| Normal | 0 | |
| Clouded | 5 | |
| Stuporous | 10 | |
| Comatose | 25 | 25 |
| Respiration | | |
| Normal | 0 | |
| Abnormal | 5 | 5 |
| Cranial nervs | | |
| Vision | 1 | |
| Light reflex | 1 | |
| Oculocephalic | 1 | |
| Corneal | 1 | |
| Facial sensation | 1 | |
| Auditory | 1 | |
| Gag reflex | 1 | 7 |
| Motor and sensory function | | |
| Flexor response to pain (Front) | 2 | |
| Flexor response to pain (Rear) | 2 | |
| Righting reflex | 10 | 14 |
| Gait | | |
| Normal | 0 | |
| Minimal ataxia | 5 | |
| Moderate ataxia | 10 | |
| Able to stand | 15 | |
| Unable to stend | 20 | |
| No purposeful movement | 25 | 25 |
| Behavior | | |
| Grooming | 4 | |
| Eating/drinking | 10 | |
| Exploring | 10 | 24 |
| Total | | 100 |

After 7 days of follow-up, surviving rabbits were reanesthetized and a pressure catheter (SciSense, London, Ontario, Canada) was introduced into the left ventricle through the right carotid artery for measurement of end-diastolic pressures as well as positive and negative left ventricular rate of pressure development ($dP/dt_{max}$ and $dP/dt_{min}$). These parameters were also measured in a group of Sham rabbits that were neither submitted to cardiac arrest nor hypothermia.

Blood Chemistry and Caspase Activity Assay

Blood pH, carbon dioxide and oxygen partial pressures ($pCO_2$ and $pO_2$, respectively) were assessed from arterial blood samples with an ABL 77 series analyser (Radio-meter SA, France). Blood lactate was determined on an Accutrend® Plus analyser (Roche Diagnostics, Mannheim, Germany). Liver and renal functions were evaluated by measuring the alanine aminotransferase (ALAT) and creatinine concentrations (Prestige 24i, Tokyo-Boehi, Japan). Troponine I and Creatinine Kinase were measured by an off-site laboratory (IDEXX Laboratories, Alfortville, France).

Caspase 3 activity was assayed from cardiac samples, as previously described ("Cardioprotection against myocardial infarction with PTDBIR3/RING, a XIAP mimicking protein", Souktani R, Pons S, Guegan C, Bouhidel O, Bruneval P, Zini R, Mandet C, Onteniente B, Berdeaux A, Ghaleh B, J Mol Cell Cardiol, 2009; 46:713-718). Briefly, tissues were homogenized in cold buffer (25 mM HEPES pH 7.5, 5 mM $MgCl2$, 2 mM EDTA, 0.1% Triton X-100, 2 mM dithiothreitol, 1 mM PMSF, 5 µl/ml protease cocktail inhibitor P8340; Sigma-Aldrich, St Louis, Mo., USA). Homogenates were centrifuged and supernatants collected. Proteins (90 µg) were incubated in caspase assay buffer (50 mM HEPES pH 7.4, 100 mM NaCl, 1 mM EDTA, 10 mM dithiothreitol, Triton X-100 0.1%, glycerol 10%). Enzymatic reaction was started by addition of 0.2 mM of the fluorogenic substrates ac-DEVD-AFC (Biomol Research Laboratories, Hambourg, Germany). Fluorescent arbitrary units were converted into pmol/mg protein/h using a standard curve of free AFC (Biomol Research Laboratories, Hambourg, Germany).

Histological Analyses

After 7 days of follow-up after cardiac arrest, the surviving rabbits were finally euthanized for pathological analyses of the heart, lung, kidney, liver and brain. These organs were also removed and analyzed in the animals died before the end of the follow-up. For lungs, a slice was sampled from each lobe (5 per lung). For the heart, a mid heart transversal biventricular section has been analysed. For kidneys, two slices were studied for each organ. A 0-3 score system has been used to blindly quantify the severity of each organ alteration, as shown in Supplemental Table 2 providing a histological cerebral lesion severity grading scale, and Supplemental Table 3 providing histological lesion severity grading scale for kidney, liver, heart and lung (0=normal; 3=very severe lesion).

SUPPLEMENTAL TABLE 2

| | Score |
|---|---|
| Neocortex | |
| Normal | 0 |
| Rare ischemic neurons (<10%) | 1 |
| Frequent ischemic neurons (10-50%) | 2 |
| Majority of neurons ischemic (>50%) | 3 |
| Hippocampus | |
| Normal | 0 |
| Rare ischemic pyramidal or granule cells | 1 |
| Focal ischemic damage | 2 |
| Severe, diffuse ischemic damage | 3 |
| Cerebellum | |
| Normal | 0 |
| Rare ischemic Purkinje cells | 1 |
| 10-50% ischemic Purkinje cells | 2 |
| >50% ischemic Purkinje cells | 3 |

SUPPLEMENTAL TABLE 3

| | Score |
|---|---|
| Kidney | |
| Normal | 0 |
| Dilated regenerative proximal tubule | 1 |
| Focal scar fibrosis | 2 |
| Extensive scar fibrosis | 3 |
| Liver | |
| Normal | 0 |
| Limited clarification of hepatocytes | 1 |
| Moderate clarification of hepatocytes | 2 |
| Extensive clarification of hepatocytes | 3 |
| Heart | |
| Normal | 0 |
| Very rare foci of cardiomyocyte necrosis | 1 |
| Rare foci of cardiomyocyte necrosis | 2 |
| Frequent foci of cardiomyocyte necrosis | 3 |
| Lung (cardiogenic lesion) | |
| Normal | 0 |
| Limited congestion and/or serous edema | 1 |
| Moderate congestion and/or serous edema | 2 |
| Extended congestion and/or serous edema | 3 |
| Lung (infection) | |
| Normal | 0 |
| Limited foci of bronchopneumia | 1 |
| Moderate foci of bronchopneumia | 2 |
| Extended foci of bronchopneumia | 3 |

Figure 6:
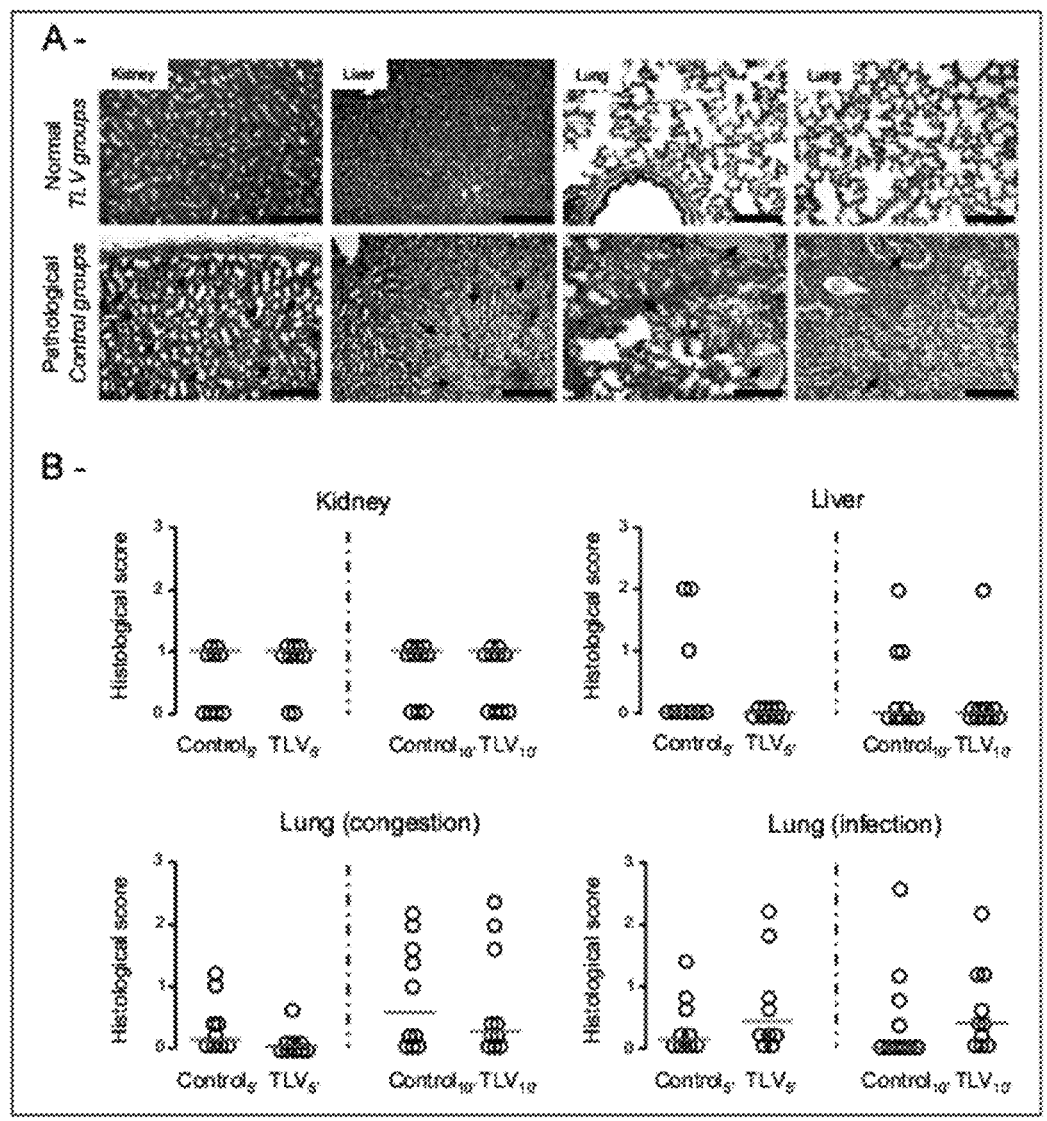
Figure 7:
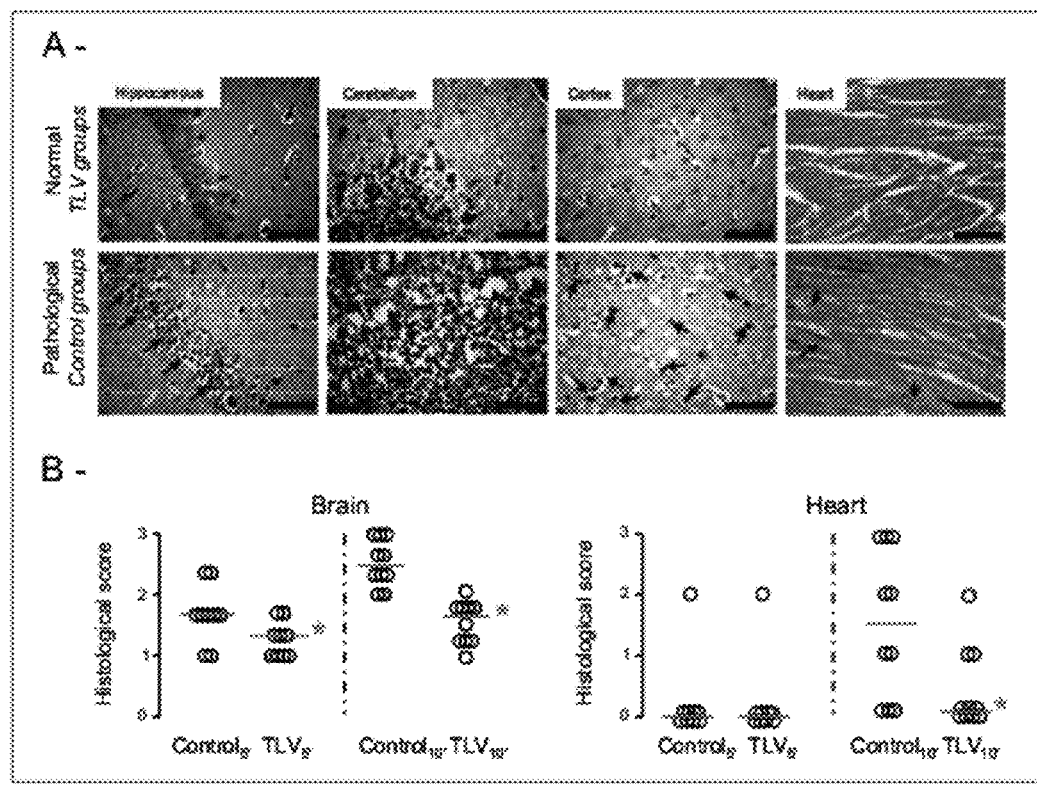

The overall brain score was the mean value obtained for cortex, hippocampus and cerebellum, as previously described ("Hypothermia prevents ischemia-induced increases in hippocampal glycine concentrations in rabbits", Baker A J, Zornow M H, Grafe M R, Scheller M S, Skilling S R, Smullin D H, Larson A A, Stroke, 1991; 22:666-673). For lungs, two separate scores for cardiogenic lesions (serous edema and/or congestion) and infectious complication of bronchopneumonia, respectively, have been assessed. Panels A of FIGS. 6 and 7 illustrate examples of typical normal or pathological histological appearances of the kidney, liver, lungs, brain (hippocampus, cerebellum and cortex) and heart in the TLV and Control groups.

Statistical Analyses

Data were expressed as mean±SEM. Hemodynamic and biochemical parameters were compared between TLV groups and corresponding Controls using a two-way ANOVA for repeated measures. Post-hoc analyses were performed at each time-point between TLV and Controls using a Student t-test with Bonferonni correction. Values were not compared between the different time-points in order to avoid multiple comparisons. Neurological dysfunction and histological scores were compared between TLV groups and corresponding Controls using a Mann-Whitney non parametric test. Survival curves were obtained using a Kaplan-Meier analysis and were compared between groups using a log-rank test. Significant differences were determined at $P \leq 0.05$.

Results

Fifty rabbits were included in the present study and submitted to cardiac arrest (n=10, 10, 15 and 15 in the $Control_{5'}$, $TLV_{5'}$, $Control_{10'}$ and $TLV_{10'}$ groups, respectively).

Cardiac Arrest and Resuscitation

Table 1 below gathers group characteristics during cardiopulmonary resuscitation, including the rate of successful resuscitation, the time to resumption of spontaneous circulation (ROSC) and the total amount of epinephrine administered throughout the protocol.

TABLE 1

| | n | Rate of successfull resuscitation | ROSC (min) | Epinephrine dose (µg/kg) |
|---|---|---|---|---|
| $Control_{5'}$ | 10 | 10/10 | 2.4 ± 0.3 | 207 ± 58 |
| $TLV_{5'}$ | 10 | 10/10 | 2.3 ± 0.3 | 174 ± 81 |
| $Control_{10'}$ | 15 | 10/15 | 4.8 ± 0.4 | 684 ± 118 |
| $TLV_{10'}$ | 15 | 10/15 | 4.2 ± 0.8 | 128 ± 128 * |

TLV, total liquid ventilation;
* p < 0.05 vs corresponding Control value.

As shown in Table 1, all rabbits subjected to 5 minutes of cardiac arrest were successfully resuscitated ($Control_{5'}$ and $TLV_{5'}$ groups) whereas only 10/15 were successfully resuscitated in the $Control_{10'}$ and $TLV_{10'}$ groups, respectively. Regardless the duration of the cardiac arrest, the time to resumption of spontaneous circulation was not significantly different between TLV groups and corresponding Controls.

Hypothermic TLV Affords a Generalized Ultra-Fast Cooling after Resuscitation

Figure 3:
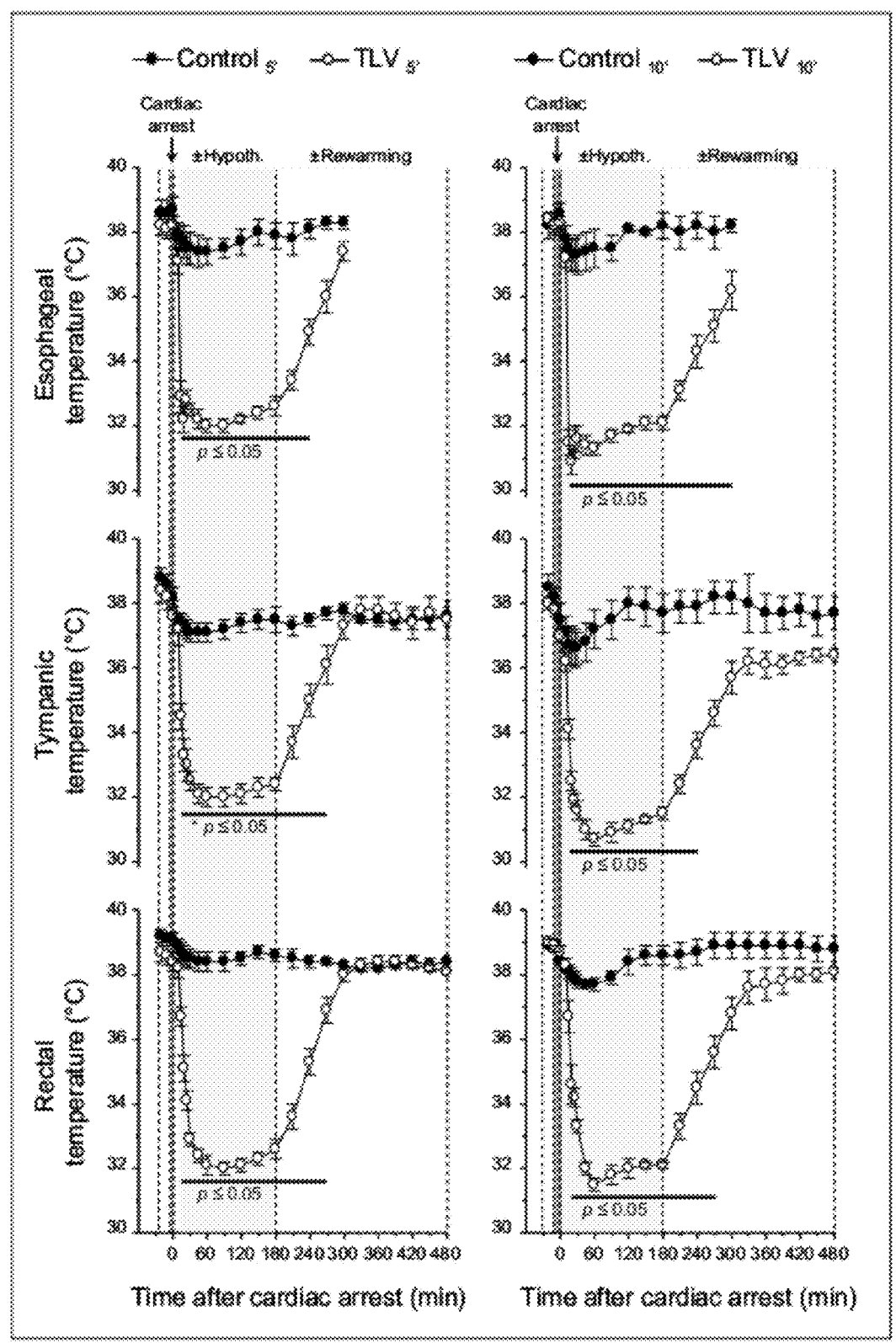

As illustrated in FIG. 3, esophageal, tympanic and rectal temperatures were not significantly different among groups at baseline. A mild and passive decrease in body temperature was observed in the $Control_{5'}$ and $Control_{10'}$ groups after cardiac arrest but this remained within the normothermic range. In TLV groups, esophageal and tympanic temperatures decreased very rapidly after the institution of TLV. As example, tympanic temperature achieved 33.3±0.5 and 32.5±0.3° C. in $TLV_{5'}$ and $TLV_{10'}$ within 10 minutes after the onset of the cooling protocol, respectively.

Hypothermic TLV Improves Hemodynamic by Decreasing the Need in Epinephrine

Table 2 below gathers data as regards to mean arterial pressure and heart rate throughout the experimental protocol in the different groups.

TABLE 2

| | | | Cardiopulmonary resuscitation | | | | | |
|---|---|---|---|---|---|---|---|---|
| | n | Baseline | 15 min | 60 min | 180 min | 360 min | 480 min | Day 1 (n) |
| Epinephrine perfusion | | No | Yes | Yes | Yes | Yes | No | |
| Heart rate (beat/min) | | | | | | | | |
| $Control_{5'}$ | 10 | 257 ± 11 | 222 ± 8 | 221 ± 7 | 243 ± 11 | 216 ± 7 | 220 ± 9 | 234 ± 8 (10) |
| $TLV_{5'}$ | 10 | 259 ± 10 | 202 ± 12 | 174 ± 6* | 177 ± 9* | 245 ± 9 | 234 ± 8 | 244 ± 10 (10) |
| $Control_{10'}$ | 10 | 263 ± 10 | 219 ± 6 | 220 ± 10 | 198 ± 8 | 221 ± 11 | 231 ± 13 | 256 ± 17 (7) |
| $TLV_{10'}$ | 10 | 267 ± 8 | 167 ± 10* | 158 ± 8* | 167 ± 11 | 208 ± 12 | 240 ± 11 | 252 ± 7 (8) |

TABLE 2-continued

|  | | | Cardiopulmonary resuscitation | | | | | |
|---|---|---|---|---|---|---|---|---|
|  | n | Baseline | 15 min | 60 min | 180 min | 360 min | 480 min | Day 1 (n) |
| Mean arterial pressure (mmHg) | | | | | | | | |
| Control$_{5'}$ | 10 | 81 ± 3 | 83 ± 4 | 82 ± 3 | 83 ± 1 | 83 ± 4 | 80 ± 4 | 83 ± 4 (10) |
| TLV$_{5'}$ | 10 | 80 ± 7 | 81 ± 3 | 82 ± 5 | 82 ± 3 | 83 ± 3 | 79 ± 3 | 82 ± 4 (10) |
| Control$_{10'}$ | 10 | 80 ± 5 | 82 ± 3 | 83 ± 3 | 81 ± 4 | 83 ± 2 | 80 ± 3 | 79 ± 4 (7) |
| TLV$_{10'}$ | 10 | 83 ± 4 | 81 ± 4 | 82 ± 3 | 81 ± 3 | 81 ± 4 | 80 ± 4 | 79 ± 6 (8) |

TLV, total liquid ventilation;
*p < 0.05 vs corresponding Control value.

As shown in Table 2, heart rate significantly decreased during the hypothermic phase in TLV groups as compared to corresponding Controls (e.g., −21% and −28% at 60 minutes after cardiac arrest in TLV$_{5'}$ and TLV$_{10'}$ Vs Control$_{5'}$ and Control$_{10'}$, respectively). Mean arterial pressure was not significantly different between groups throughout the experimental protocol since epinephrine administration was permitted to maintain an about 80 mmHg value during 7 hours after cardiac arrest. As shown in Table 1, the total amount of epinephrine administered throughout cardiopulmonary resuscitation was however significantly lower in TLV$_{10'}$ Vs Control$_{10'}$ (128±128 Vs 684±118 µg/kg, respectively), suggesting a favourable hemodynamic effect of hypothermic TLV. No such a significant difference has been observed in TLV$_{5'}$ Vs Control$_{5'}$ but epinephrine dosages were much lower (174±81 Vs 207±58 µg/kg, respectively). After discontinuation of any pharmacological support (e.g., at 8 hour after cardiac arrest), the lactate levels significantly decreased in TLV$_{5'}$ Vs Control$_{5'}$ (1.2±0.2 Vs 4.8±1.7 mmol/l) and in TLV$_{10'}$ Vs Control$_{10'}$ (3.6±0.7 Vs 7.0±1.7 mmol/l).

Figure 4:
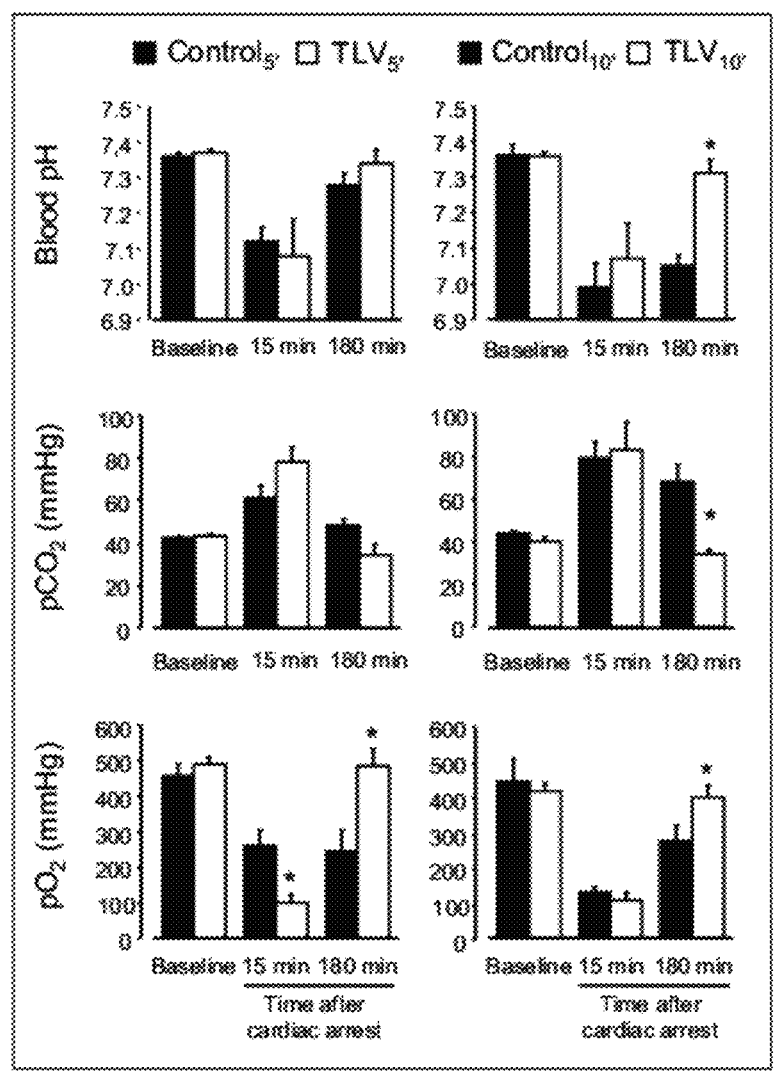

Hypothermic TLV is Safe for the Lungs and does not Alter Kidney and Liver Function As shown in FIG. 4, a severe acidosis with an increase in pCO$_2$ and a decrease in pO$_2$ in all groups following cardiac arrest has been observed. In TLV$_{5'}$, pO$_2$ was lower 15 minutes after cardiac arrest as compared to Control$_{5'}$. This could be expected as Control animals were ventilated with oxygen whereas TLV rabbits underwent liquid ventilation by that time. At 180 minutes, gas exchanges were conversely improved in TLV groups as compared to Controls. As example, blood pH and pO$_2$ increased whereas pCO$_2$ decreased in TLV$_{10'}$ Vs Control$_{10'}$, respectively. Importantly, all the animals were submitted to conventional ventilation at that time point, with standardized ventilation parameters.

On FIG. 6, panel A provides examples of normal or pathological histological appearances of the kidney, liver and lungs in the TLV and Control groups, respectively. In kidney, lesions consisted in dilated regenerative proximal tubules (arrows, bar=120 µm). In liver, systematized clarification of hepatocytes (arrows, bar=120 µm) have been observed. In lungs, lesions were congestion and serous edema (arrows in the left lung panel, bar=120 µm) or foci of bronchopneumonia (arrows in the right lung panel, bar=120 µm). Panel B provides histological scores of alteration in kidney, liver and lungs of rabbits from the different groups. For lungs, two separate scores for cardiogenic lesions and infection complications, respectively, have been assessed.

As illustrated in FIG. 6, the safety of TLV for lungs was also documented by histology demonstrating cardiogenic lesions (serous edema and/or congestion) or infectious complications of bronchopneumonia to a similar extent in TLV groups Vs corresponding Controls.

Table 3 below gathers data as regards to plasma creatinine and alanine aminotransferase concentrations (ALAT) in the different groups.

TABLE 3

|  | | | Time following cardiac arrest | | |
|---|---|---|---|---|---|
|  | n | Baseline | 15 min | 180 min | Day 1 |
| Plasma creatinine concentrations (mg/l) | | | | | |
| Control$_{5'}$ | 10 | 10 ± 1 | 11 ± 1 | 10 ± 1 | 10 ± 1 (10) |
| TLV$_{5'}$ | 10 | 10 ± 0 | 12 ± 1 | 11 ± 1 | 10 ± 1 (10) |
| Control$_{10'}$ | 10 | 9 ± 1 | 13 ± 1 | 14 ± 2 | 11 ± 1 (7) |
| TLV$_{10'}$ | 10 | 10 ± 0 | 13 ± 1 | 12 ± 1 | 11 ± 1 (8) |
| Plasma ALAT concentrations (UI/l) | | | | | |
| Control$_{5'}$ | 10 | 29 ± 5 | 31 ± 4 | 33 ± 4 | 35 ± 9 (10) |
| TLV$_{5'}$ | 10 | 25 ± 3 | 26 ± 2 | 43 ± 5 | 30 ± 6 (10) |
| Control$_{10'}$ | 10 | 44 ± 13 | 79 ± 25 | 115 ± 32 | 60 ± 17 (7) |
| TLV$_{10'}$ | 10 | 48 ± 3 | 65 ± 5 | 111 ± 27 | 83 ± 14 (8) |

TLV, total liquid ventilation;
ALAT, alanine aminotransferase.

As shown in Table 3, renal function was not affected after cardiac arrest in all groups since plasma creatinine levels remained within usual values. Conversely, we observed an increase in the liver enzyme ALAT with no difference among TLV and corresponding Controls. Kidney and liver lesions were mild with no difference between TLV and Controls (FIG. 6).

Figure 5:
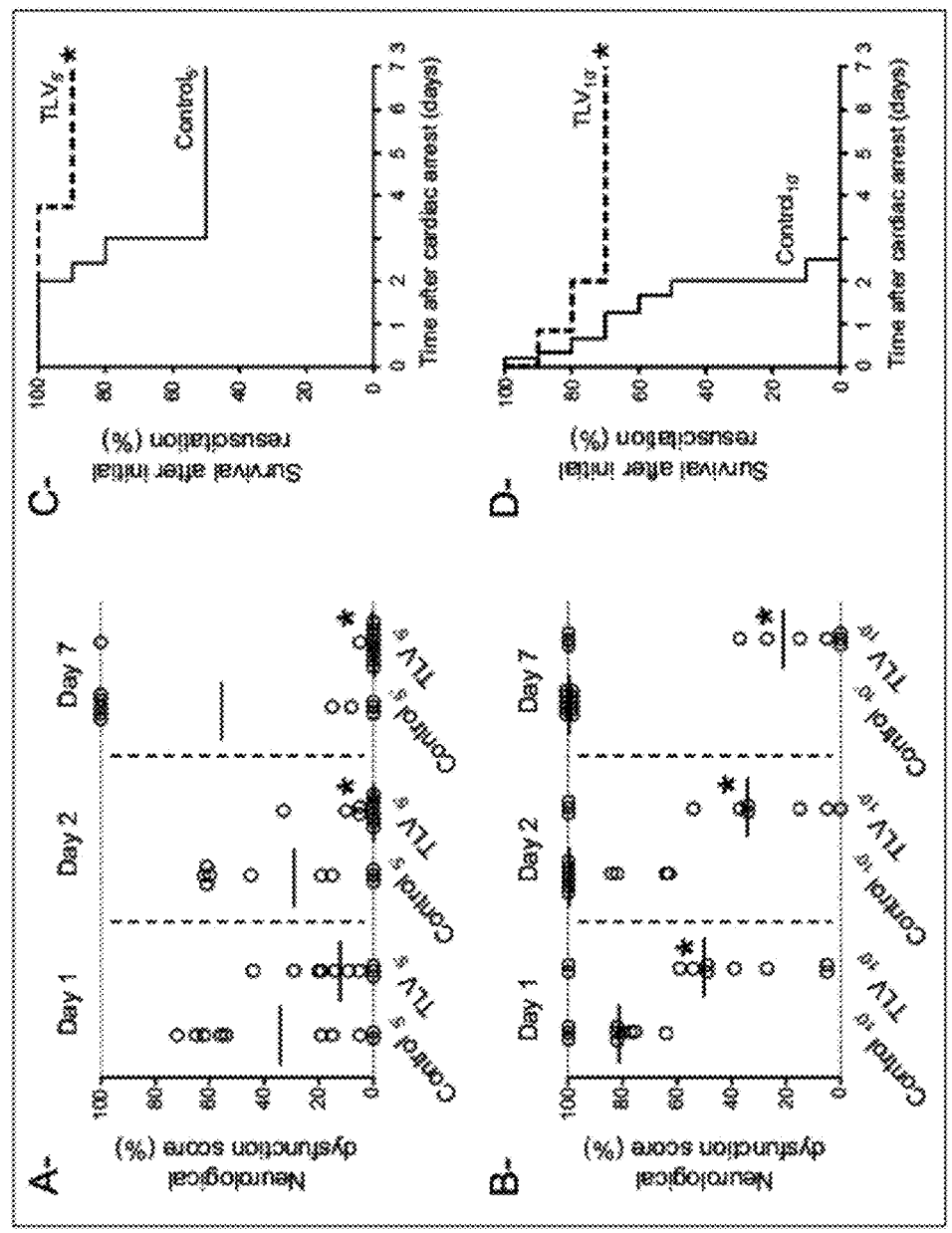

Hypothermic TLV Improves Neurological Functional Recovery, Increases Survival and Preserves Histological Brain Integrity As illustrated in FIG. 5, neurological dysfunction was significantly attenuated in TLV groups as compared to Controls. This difference was significant as early as the 2$^{nd}$ day following cardiac arrest in TLV$_{5'}$ Vs Control$_{5'}$ (panel A) whereas this was observed within 24 hours of follow-up in TLV$_{10'}$ Vs Control$_{10'}$ (panel B).

A significant difference in survivals was also evidenced between TLV groups and corresponding Controls, as illustrated in FIG. 5 (panels C and D). At the end of the follow-up, 9/10 and 7/10 rabbits survived in the TLV$_{5'}$ and TLV$_{10'}$ groups as compared to 5/10 and 0/10 in Control$_{5'}$ and Control$_{10'}$, respectively.

On FIG. 7, panel A provides examples of normal or pathological histological appearances of the brain and the heart in the TLV and Control groups, respectively. In brain, ischemic disorders consisted in ischemic pyramidal cells with pycnotic nucleus in the hippocampus (arrows, bar=30 μm), in laminar necrosis of Purkinje cells in the cerebellum (arrows, bar=30 μm) or in numerous ischemic neurons in the cortex (arrows, bar=30 μm), respectively. In the myocardium, we observed foci of cardiomyocytes necrosis (arrows, bar=120 μm). Panel B provides histological scores of alteration in the brain and heart of rabbits from the different groups.

As illustrated in FIG. 7, the neuroprotective effect of TLV was further demonstrated by a significant decrease in the severity of the ischemic disorders in the brain in both TLV groups as compared to Control.

Hypothermic TLV Preserves Cardiac Histological Integrity and Protects Against Early Cardiac Cell Death after Cardiac Arrest As illustrated in FIG. 7, myocardial foci of necrosis were less frequent in $TLV_{10'}$ Vs $Control_{10'}$, demonstrating a cardioprotective effect of TLV. In surviving animals, the functional myocardial sequels of cardiac arrest were also evaluated after 7 days of follow-up.

Supplemental Table 4 below provides hemodynamic parameters in surviving rabbits after 7 days following cardiac arrest.

SUPPLEMENTAL TABLE 4

|  | n | Conscious state | Anesthesia |
|---|---|---|---|
| Heart rate (beat/min) | | | |
| Sham | 5 | 254 ± 19 | 282 ± 9 |
| $Control_{5'}$ | 5 | 219 ± 14 | 261 ± 17 |
| $TLV_{5'}$ | 9 | 258 ± 18 | 261 ± 18 |
| $Control_{10'}$ | 0 | — | — |
| $TLV_{10'}$ | 7 | 230 ± 14 | 273 ± 34 |
| Mean arterial pressure (mmHg) | | | |
| Sham | 5 | 81 ± 8 | 82 ± 4 |
| $Control_{5'}$ | 5 | 98 ± 11 | 83 ± 5 |
| $TLV_{5'}$ | 9 | 100 ± 2 | 93 ± 7 |
| $Control_{10'}$ | 0 | — | — |
| $TLV_{10'}$ | 7 | 94 ± 6 | 94 ± 10 |
| End diastolic left ventricular pressure (mmHg) | | | |
| Sham | 5 | — | 3.6 ± 0.6 |
| $Control_{5'}$ | 5 | — | 3.3 ± 0.8 |
| $TLV_{5'}$ | 9 | — | 3.8 ± 1.1 |
| $Control_{10'}$ | 0 | — | — |
| $TLV_{10'}$ | 7 | — | 2.7 ± 0.5 |
| $dP/dt_{max}$ (mmHg/s) | | | |
| Sham | 5 | — | 7182 ± 1313 |
| $Control_{5'}$ | 5 | — | 7455 ± 927 |
| $TLV_{5'}$ | 9 | — | 7132 ± 1157 |
| $Control_{10'}$ | 0 | — | — |
| $TLV_{10'}$ | 7 | — | 6518 ± 1958 |
| $dP/dt_{min}$ (mmHg/s) | | | |
| Sham | 5 | — | −5364 ± 914 |
| $Control_{5'}$ | 5 | — | −6156 ± 1251 |
| $TLV_{5'}$ | 9 | — | −6107 ± 758 |
| $Control_{10'}$ | 0 | — | — |
| $TLV_{10'}$ | 7 | — | −6323 ± 1426 |

TLV: total liquid ventilation;
$dP/dt_{max}$: maximal positive left ventricular rate of pressure development;
$dP/dt_{min}$: maximal negative left ventricular rate of pressure development.

As shown in Supplemental Table 4, mean blood pressure and heart rate in the conscious state were not different among groups as compared to a Sham group. After anaesthesia, end diastolic left ventricular pressure, $dP/dt_{max}$ and $dP/dt_{min}$ were also not different between groups, suggesting that there was no major functional myocardial alteration in those surviving animals.

Figure 8:
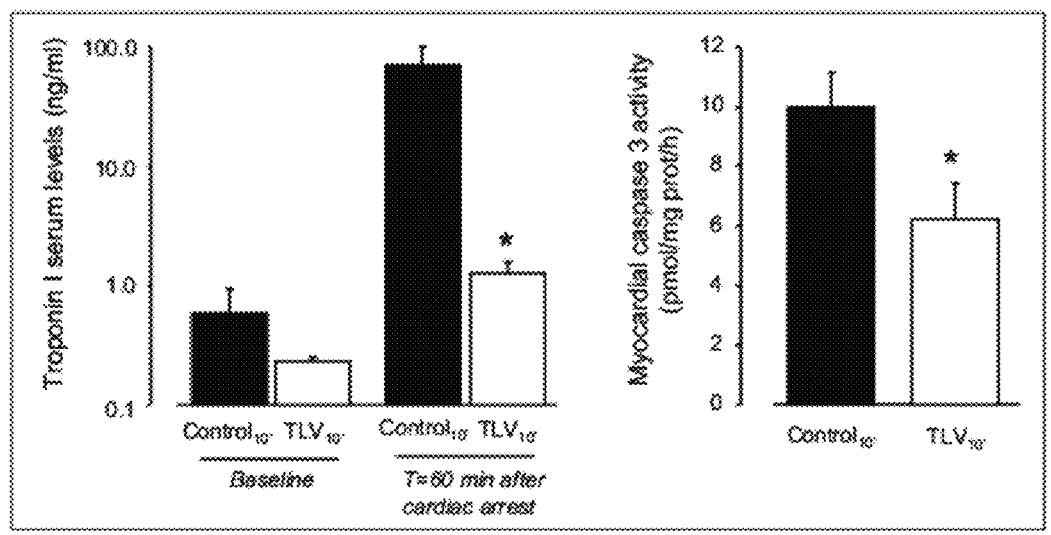

To further explore the cardioprotective effect of TLV, eight additional rabbits were included in the $Control_{10'}$ and $TLV_{10'}$ groups for a surrogate study dedicated to the caspase activity assays and measurement of troponin I levels. As shown in FIG. 8 (left panel), troponine I measured 60 minutes after cardiac arrest significantly decreased in $TLV_{10'}$ as compared to $Control_{10'}$ (1.3±0.3 Vs 70.7±30.4, respectively). The cardioprotective effect of TLV was also supported by a decrease in caspase 3 activity as compared to Control (FIG. 8, right panel).

Discussion

The present study provides the proof of concept that ultra-fast whole body cooling with TLV limits the post-cardiac arrest syndrome when instituted after ROSC in a rabbit model of ventricular fibrillation. Interestingly, potent neuro- and cardioprotections have been observed with TLV which remains a safe procedure for the lungs. As hypothermia has been performed for 3 hours, this also suggested that very early hypothermia after ROSC does not need to be prolonged to produce a strong clinical benefit.

The study shows the rapidity of TLV-induced cooling since oesophageal and brain temperatures achieved about 32-33° C. within only 10 minutes. In comparison, an external cooling with cold blankets was previously shown to require at least 60 minutes to achieve a similar target temperature in equally sized rabbits ("Rapid cooling of the heart with total liquid ventilation prevents transmural myocardial infarction following prolonged ischemia in rabbits", Chenoune M, Lidouren F, Ghaleh B, Couvreur N, Dubois-Rande J-L, Berdeaux A, Tissier R, Resuscitation, 2010; 81:359-362). The rapid cooling elicited by TLV was directly related to the tidal exchange of the liquid since simple repetitive pulmonary lavages with a 4° C. perfluorocarbon requires more than 60 minutes to decrease the tympanic temperature to 32° C. in the same species ("Cold perfluorochemical-induced hypothermia protects lung integrity in normal rabbits", Yang S S, Jeng M J, McShane R, Chen C Y, Wolfson M R, Shaffer T H, Biol Neonate, 2005; 87:60-65).

Importantly, the rapid hypothermia elicited by TLV was associated with a potent neurological protection and an increase in survival rate as compared to Control conditions. In animal studies, it is admitted that the neuroprotective effect of hypothermia is time dependent and that a large part of the protection is lost when cooling is delayed. For example, in a canine model of cardiac arrest, the neurological protection was lost after only 15 minutes of delay before the onset of hypothermia after ROSC ("Delay in cooling negates the beneficial effect of mild resuscitative cerebral hypothermia after cardiac arrest in dogs: a prospective, randomized study", Kuboyama K, Safar P, Radovsky A, Tisherman S A, Stezoski S W, Alexander H, Crit Care Med, 1993; 21:1348-1358). In the present study, a very potent benefit of hypothermia has been observed when achieved rapidly after ROSC. In this respect, hypothermia started before ROSC (e.g., intra-arrest hypothermia) can afford an additional benefit. All these findings demonstrate that most of the possible benefits of hypothermia can be lost within minutes after ROSC, further supporting the need of systems eliciting ultra-fast cooling such as TLV in the present study.

Importantly, the benefit of TLV observed in our conditions was produced by a short hypothermic episode (3 hours), whereas the current recommendations in humans are maintenance of hypothermia during 24-36 hours. It appears that ultra-fast hypothermia does not need to be prolonged to produce a real potent benefit whereas a delayed cooling would require a longer duration to finally afford a milder protection. Since the benefit was virtually maximal with the above described hypothermic protocol in the present study, longer duration of hypothermia would not provide any additional benefit.

Another important beneficial effect of TLV is the cardioprotection observed here. This was especially observed after 10 minutes of cardiac arrest since myocardial lesions were minor in the groups submitted to only 5 minutes of cardiac arrest. This was evidenced by a limitation in myocardial necrosis and a preservation of myocardial functional performance in surviving rabbits. Cardioprotection was also observed very early after cardiac arrest since troponine I release and caspase 3 activity were significantly decreased within 60 minutes after resuscitation in $TLV_{10'}$ Vs $Control_{10'}$. In the present study, hypothermia was instituted after global reperfusion (ROSC) but the myocardium remains momentarily and partially ischemic even after ROSC. This can explain that a very rapid cooling with TLV can still afford a beneficial effect even if instituted after ROSC and systemic reperfusion. This also supports the relevance of a rapid and generalized cooling after cardiac arrest whereas efforts to selectively increase the regional head cooling would not be similarly cardioprotective. Generalized hypothermia could even potentially afford a protection of the liver and/or the kidney.

Importantly, TLV is a safe procedure for the lungs. Even, improved gas exchanges have been observed using standardized ventilatory parameters in TLV Vs Control groups at 3 hours after cardiac arrest. After weaning from ventilation, animals were however maintained in a cage enriched in oxygen to avoid hypoxic episodes. In the study, the tolerance of TLV was shown by histological examinations and total liquid ventilation can even protect the lungs.

In conclusion, ultra-fast cooling instituted by TLV limits the post-cardiac arrest dysfunctions with associated neuro- and cardioprotective effects. Importantly, TLV is a safe procedure for the lungs. The beneficial effects of TLV are probably directly related to the rapidity in temperature decrease since myocardial cell death inhibition was evidenced even very early following resuscitation. This also shows that ultra-fast whole body hypothermia after ROSC does not need to be prolonged to produce a functional benefit.

The invention claimed is:

1. A system for treatment of a body of a mammal in cardiac arrest, comprising:
   a monitoring unit adapted to measure and to process data related to the treatment,
   a cooling device controlled by the monitoring unit to cool the body to a target temperature during a cooling time period, said cooling device being adapted to perform total liquid ventilation and comprising:
      a reservoir filled with a cooling liquid,
      a pumping arrangement adapted to alternately fill lungs of the body with the cooling liquid and remove from the lungs said cooling liquid,
   the cooling device being controlled to stop after the target temperature has been reached,
   a temperature maintaining device separate from the cooling device and controlled by the monitoring unit to maintain the body at the target temperature obtained through the implementation of total liquid ventilation for a hypothermia duration while the cooling device is stopped, wherein said temperature maintaining device comprises a ventilator adapted to perform conventional gas ventilation and controlled by the monitoring unit to instill oxygen at a desired temperature so as to maintain the body at the target temperature.

2. The system according to claim 1, wherein the cooling liquid is chosen from the group consisting of perfluorocarbons.

3. The system according to claim 1, further comprising at least one resuscitation apparatus adapted to attempt resuscitation of the mammal.

4. The system according to claim 1, wherein the temperature maintaining device further comprises an external cooling device adapted to perform heat exchange with an exterior of the body.

5. The system according to claim 1, further comprising a tube comprising a distal end intended to be arranged at the vicinity of the lungs of the body, and a proximal end intended to be arranged outside the body, and wherein the proximal end of the tube is adapted to be selectively connected to the cooling device and to the ventilator.

* * * * *